United States Patent [19]

Zomer et al.

[11] Patent Number: 6,018,047
[45] Date of Patent: Jan. 25, 2000

[54] ACRIDINIUM COMPOUNDS AS CHEMILUMINOGENIC LABEL

[76] Inventors: Gijsbert Zomer, Kromme Nieuwe Gracht 41 A Bis, 3512 He Utrecht, Netherlands; Johannus Franciscus Cornelius Stavenuiter, Gerrit van de Veenstraat 105, 3762 XK Soest, Netherlands

[21] Appl. No.: 08/478,125

[22] Filed: Jun. 7, 1995

Related U.S. Application Data

[62] Division of application No. 07/719,656, Jun. 24, 1991, Pat. No. 5,521,103, which is a continuation of application No. 07/283,604, Dec. 13, 1988, abandoned.

[30] Foreign Application Priority Data

Dec. 18, 1987 [NL]  Netherlands ............. 8703075

[51] Int. Cl.⁷ .................... C09B 15/00; C07D 219/04
[52] U.S. Cl. ................. 546/104; 546/102; 546/103
[58] Field of Search .................... 436/501, 518, 436/536, 544, 546, 548, 800, 805; 530/389.8; 546/104, 102, 103; 435/6, 7.1

[56] References Cited

U.S. PATENT DOCUMENTS

| | | | |
|---|---|---|---|
| 2,645,594 | 7/1953 | Tabern ..................... | 546/102 |
| 3,431,264 | 3/1969 | Sheehan et al. ............ | 546/103 |
| 3,539,574 | 11/1970 | Sheehan et al. ........... | 546/102 |
| 3,615,416 | 10/1971 | Fox ........................ | 546/102 |
| 4,745,181 | 5/1988 | Law et al. . | |
| 5,468,646 | 11/1995 | Mattingly et al. ......... | 436/7.1 |

FOREIGN PATENT DOCUMENTS

| | | |
|---|---|---|
| 0082636 | 12/1982 | European Pat. Off. . |
| 0103469 | 9/1983 | European Pat. Off. . |
| 0212951 | 8/1986 | European Pat. Off. . |
| 0216553 | 8/1986 | European Pat. Off. . |
| 0273115 | 7/1988 | European Pat. Off. . |
| 1461877 | 2/1974 | United Kingdom . |

OTHER PUBLICATIONS

Weeks et al., Acridinium Esters as High–Specific–Activity Labels in Immunoassay, Clin. Chem. 29:1474–1479 (1983).
Patel, et al., Homogeneous Immunoassay Based on Chemiluminescence Energy Transfer, Clinical Chemistry, (1983).
Forster, Experimentelle und theoretishe Untersuchung des zwischenmolekularen Ubergangs von Elektronenanregungsenergie Z. Naturforschg. 4a 321–327 (1949).
Abbot labs, "Acridinium Salts . . . " Chem Abstracts, 111:97109.
Forster, Zwischenmolekulare Energiewanderung und Fluoreszenz Annalen der Physik. G. Folge. Band 2 (1948).
Sargent "Carbinolamines derived from N–9 acridine" Chem. Abstracts, 52:383–384 (1958).

*Primary Examiner*—Mary E. Ceperley

[57] ABSTRACT

New acridinium compounds are provided which comply with formula 1, wherein

A is a divalent organic moiety, such as an alkylene chain,

X is a group which can be transformed together with C-9 of the acridine into a dioxetane by reaction with hydrogen peroxide, such as an aryloxy group, Y is a counter ion, and Z is a functional group, such as a carboxyl derivative.

These acridinium compounds are useful as chemiluminogenic labels for both heterogeneous and homogeneous immunoassays.

5 Claims, 2 Drawing Sheets

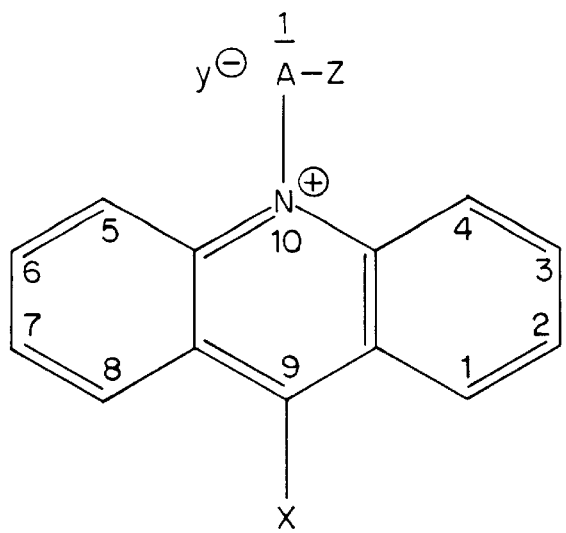
FIG. 1
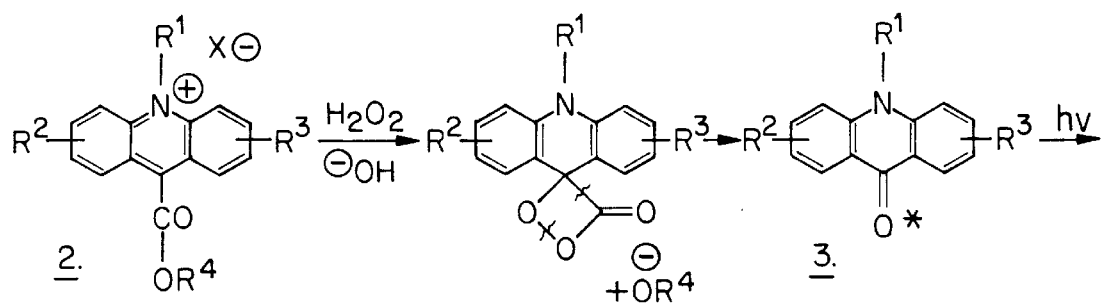
FIG. 2
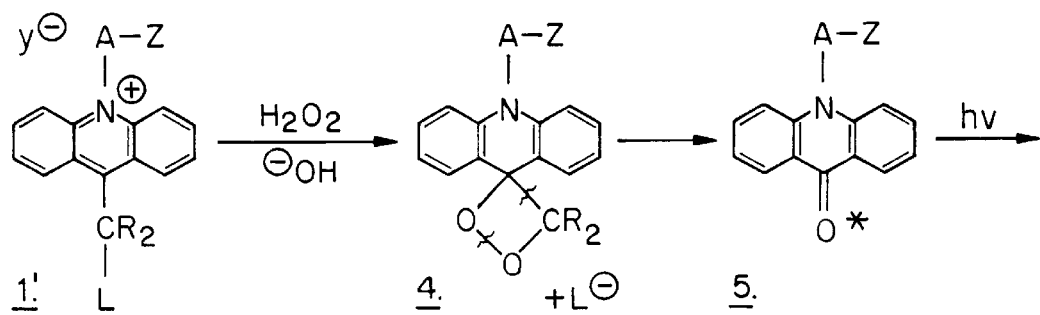

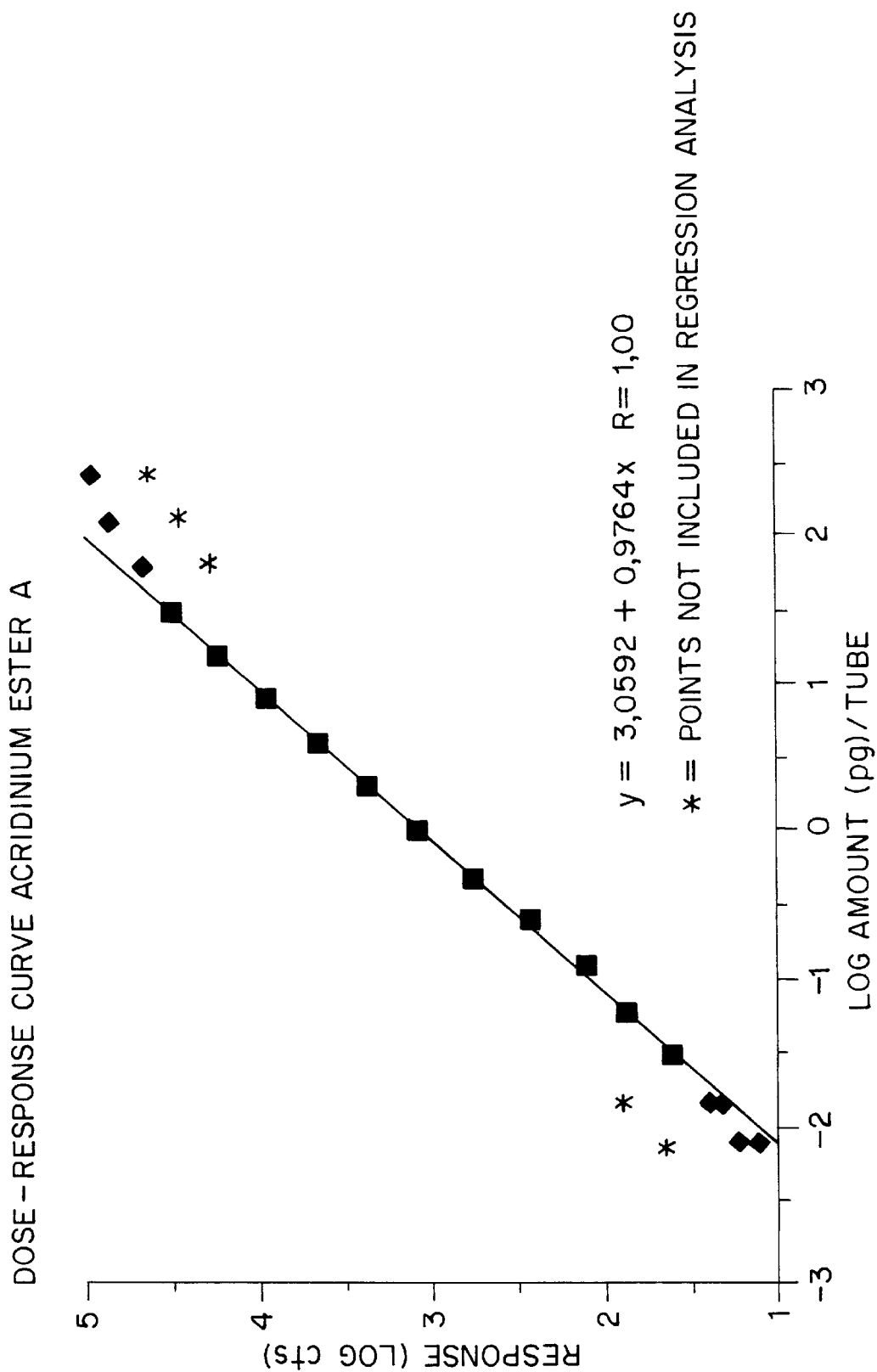

– 1 –

ACRIDINIUM COMPOUNDS AS CHEMILUMINOGENIC LABEL

This application is a division of application Ser. No. 07/719,656, filed on Jun. 24, 1991, now U.S. Pat. No. 5,521,103, which is a continuation of application Ser. No. 07/283,604, filed Dec. 13, 1988, now abandoned.

BACKGROUND OF THE INVENTION

The invention is concerned with acridinium compounds which can be used as chemiluminogenic labels.

Chemiluminogenic acridinium compounds having formula 2 wherein substituent $R^4$ contains a functional group capable of reacting with biologically interesting compounds are known from European Patent Applications 82,636 and 216,553. Labelling of nucleotides with such acridinium compounds is known from EP-A-212,951.

Chemiluminescence is the phenomenon that electromagnetic radiation (light) is emitted as a consequence of a chemical reaction. Usually, a reaction product is involved which, because of the nature of the reaction, is produced in an electronically excited state. This excited state product can revert to the "normal" ground state by losing the excess energy in the form of electromagnetic radiation. With acridinium compounds like the ones described in the European Patent Application 82,636 (see also Clin. Chem. 29 (8), 1474–1479 (1983)), chemiluminescence occurs by reaction with basic hydrogen peroxide in a way as shown schematically for compound 2 in FIG. 1.

Chemiluminogenic compounds, just like compounds containing a radioactive isotope, can be used as labels to detect substances which are labelled with these compounds. The advantages of chemiluminogenic labels over radioactive ones are the smaller health hazard, the higher sensitivity, and the longer shelf life.

The use of this kind of labels is particularly relevant in biological systems. In this way not only proteins, carbohydrates, nucleic acids, and other biologically relevant compounds can be determined, but it is also possible to monitor the biological reactions of these compounds with suitable reaction partners. Examples include the interaction of a drug with its receptor, of a toxin with its receptor or antidote, and, more specifically the immunological antigen-antibody reaction.

A special assay system which uses the chemiluminescence reaction is a system wherein the energy of the excited state product (the donor) is not directly emitted as light, but is transferred radiationless to a suitable acceptor, e.g. a fluorogenic compound. This acceptor is capable of losing this energy as electro-magnetic radiation with a wavelength differing from the wavelength of the donor chemiluminescence. This phenomenon has been described by e.g. T. Förster (Ann. Phys. (Leipzig) 2, 55–75 (1948) and Z. Naturforsch. 4a, 321–334 (1949)). Because the wavelength of the emitted light is specific for the acceptor or the donor-acceptor complex, the acceptor which might be an antibody labelled with a fluorogenic compound or a donor-complexed substrate (e.g. an antigen) can be determined without the necessity of separating the bound complex. This so-called homogeneous chemiluminescence energy transfer assay has been described using isoluminol derivatives as the label, see A. Patel and A. K. Campbell, Clin. Chem. 29 (9), 1604–1608 (1983). However, a drawback of luminol and isoluminol and derivatives is their relatively low quantum yield; moreover, a catalyst is needed to start the chemiluminescence reaction of these compounds.

A disadvantage of the acridinium compounds described in the European Patent Applications 82,836 and 216,553) is that they are not useful to perform homogeneous immunoassays based on energy transfer chemiluminescence. Another disadvantage of those prior art compounds is their limited stability in biological fluids.

Now, a class of chemiluminogenic compounds has been found which are useful as labels both for heterogeneous and homogeneous biological assays like immunoassays, and which have an enhanced stability.

The acridinium compounds according to the invention are characterized by the formula 1, wherein A is a divalent organic moiety, X is a substituent which can form a dioxetane together with he C-9 acridine atom and hydrogen peroxide, Y is a counter ion, and Z is a functional group, and wherein the benzene rings may carry one or more substituents, such as lower alkyl, lower alkoxy, halogen, etc.

On the one hand, the compounds according to the invention have a chemiluminogenic function, i.e. they can be transformed by a chemical reaction into an electronically excited state product which loses its excess of energy in the form of light. This function is present at C-9 of the acridine. On the other hand, they have a coupling function, i.e. they possess via an organic spacer a functional group capable of binding with e.g. biologically active substances like proteins, but also with e.g. toxicologically relevant compounds. The coupling function is situated on the acridine nitrogen atom. By this twofold function the compounds are useful as label, e.g. for immunoassay purposes. By a specific coupling with the analyte or with a reagent to determine the analyte the presence of the coupling product or of the interaction with the reagent can be detected using chemiluminescence.

The advantage of the acridinium compounds according to the invention is the fact that during the chemiluminescence reaction i.e. the reaction with hydrogen peroxide to give an excited acridone via a dioxetane, the coupling of emitter and analyte is maintained. As a result the energy of the excited state product can be transferred to an acceptor e.g. fluorescein and Lucifer Yellow which is present elsewhere in the coupling product or the complex. In this case the energy transfer is more efficient than with chemiluminescence donors of the isoluminol type, and furthermore, no catalyst is required to start the chemiluminescence.

A further advantage of the compounds according to the invention is the fact that the cause of the chemiluminescence reaction of the coupling product (a compound e.g. a biologically active compound like a steroid labelled with the acridinium compound) is dependent on the presence of a compound which reacts with the labelled compound e.g. an antibody or antidote. With immune reactions of this sort the kinetics of the chemiluminescence of the immune complex differs from the kinetics of the chemiluminescence of the non-complexed labelled compound (For a related case see European Patent Application 103,469). This may be determined as a change in time of maximal emission of chemiluminescence. According to this mechanism there is no need to separate the immune complexes resulting also in a homogeneous immunoassay.

The divalent organic moiety A functions as a so-called spacer, bridging the distance between acridinium moiety and functional group of the substrate. This substrate is bound by way of group Z. The length of A is such that reaction of functional group Z with a functional group of the substrate is possible. This minimal length is therefore dependent upon the substrate which has to be coupled with the compound represented by formula 1. The nature of group A is not important as long as this group does not interfere with the reactivity of functional group Z or with the desired reaction of group X with hydrogen peroxide. The moiety A may contain alkylene groups, arylene groups, carbonyl groups, heteroatoms like nitrogen, oxygen and sulfur etc., e.g. combined in the form of ester groups, thioester groups, amide groups etc. The group A may also be built from bifunctional units e.g. dicarboxylic acids, dithiols, hydroxy-acids, aminoacids, thioacids etc.

Although group A may be any non-interfering divalent organic moiety, in the preferred embodiment of the invention to avoid complicated synthetic steps a simple organic residue is chosen like a divalent hydrocarbon moiety which may contain one or more hetero-atoms and/or carbonyl groups. More specifically, A is an alkylene moiety with 1–4 carbon atoms.

X may be any group capable of forming a 1,2-dioxetane after reaction with hydrogen peroxide. In addition to the two oxygen atoms originating from hydrogen peroxide, this dioxetane contains also the C-9 atom of the acridine. This is why group X has to be a carbon atom substituted with a group capable of leaving e.g. as a negatively charged ion upon reaction with hydrogen peroxide. Examples of substitution groups include a halogen atom, an alkoxy, aryloxy, sulfonamido or alkylthio group, or an ammonium or sulfonium group. Examples of group X include 1-haloalkyl, 1-alkoxyalkyl, cyano, etc. Preferentially, group X is a alkoxycarbonyl or an activated carbamoyl group or more specifically an aryloxycarbonyl group or an arylsulfonylcarbamoyl group.

The anion Y can be any anion like halogen, sulfate, arenesulfonate, etc. As an example Y may be the ion which acts as the leaving group during the quaternization reaction at the acridine nitrogen atom.

The group Z is a functional group capable of coupling with an organic substrate. The choice of Z depends on the functional groups present in the substrate. If the substrate contains e.g. amino groups, hydroxy groups, or mercapto groups, then Z may be a carboxyl group or a reactive derivative thereof, e.g. an ester, acid chloride, etc. Coupling is then achieved by formation of a (thio)ester or (thio)amide bond. A suitable group which is also used in European Patent Application 82,636 is the N-succinimidyloxycarbonyl group. Z may also be isocyanate or isothiocyanate; coupling is then achieved in the form of a urea or urethane, or of a mono- or dithio analogue thereof. Other possible Z groups capable of reacting with amino, hydroxy, and/or mercapto groups include halides, optionally activated at the β-position by a carbonyl or alkene functional group, derivatives of sulfonic acids and phosphoric acids, azides, and optionally protonated carboximidates.

If the substrate contains carboxyl groups or derivatives thereof e.g. esters, then Z may be e.g. an amino function.

The most preferred compounds are acridinium compounds having formula 1 wherein Z is a carboxyl group or a reactive derivative thereof.

The compounds according to the invention can be prepared by per se known methods. The starting material may be acridine or an acridine suitably substituted at position 9, e.g. acridine-9-carboxylic acid, or a derivative thereof, 9-halomethyl-, 9-alkoymethyl-, or 9-aryloxymethylacridine. The acridine-9-carboxylic acid may then be transformed into a suitable ester or acylated sulfon-amide or into another derivative capable of forming a dioxetane after reaction with hydrogen peroxide. This 9-substituted acridine compound may then be quaternized at the acridine nitrogen atom, whereafter spacer A may be built, and consequently a unit carrying group Z may be incorporated. More specifically, the acridine nitrogen atom may be quaternized with the group A–Z wherein the acridine is reacted with a compound Y'-A-Z, wherein Y' is a reactive group e.g. a halogen atom, or another leaving group. It may be profitable to protect the functional group Z during the synthesis to avoid unwanted reactions. Protection of group Z may be performed in a known way: If Z is a carboxyl group this group may be protected in the form of an ester e.g. tert.butyl, benzyl, succinimidyl ester etc.

The acridinium compounds according to the invention show chemiluminescence after reaction with hydrogen peroxide according to the scheme shown in FIG. 2.

The group X is represented in FIG. 2 as the group $CR_2L$ wherein the groups R are each e.g. hydrogen or alkyl, or together form an oxo group, and L is a leaving group e.g. a halogen atom, an aryloxy group, a sulfonamido group or an ammonium group etc. Upon reaction with hydrogen peroxide and base acridinium compound 1' is transformed into the spirodioxetane 4 with the elimination of the group L. This dioxetane or dioxetanone loses a molecule of $CR_2=O$ and produces the excited state acridone with formula 5 which returns to the ground state with light emission. The chemiluminescence can be measured with known instruments, e.g. the LUMAC Biocounter 2010.

The compounds represented by formula 1 show chemiluminescence with a wavelength of generally 420 nm after reaction with hydrogen peroxide. The compound wherein the group X (=$CR_2L$) equals a phenoxycarbonyl group and the group A–Z equals a carboxymethyl group, shows chemiluminescence with a wavelength of 420 nm after reaction with hydrogen peroxide. The detection limit of this compound is lower than 8 fg (=$8.10^{-15}$ g) corresponding with about 16 attomol (=$16.10^{-18}$ mol). As is known the chemiluminescence can have analytical applications. If the compound 1 is coupled as a label to a substrate, and this coupling product is separated from non-coupled acridinium compound, then the intensity of the chemiluminescence upon reaction with hydrogen peroxide is a measure of the concentration of the coupling product, which can be related to the quantity of substrate.

The invention also relates to the use of acridinium compounds represented by formula 1 in immunoassays by means of chemiluminescence.

Herein the chemiluminogenic compound 1 is coupled to a compound that is involved in an immunological reaction, e.g. an antigen. This labelled antigen yields a labelled complex after complexing or other interaction with a compound that is also involved in an immunological reaction, e.g. an antibody. This labelled complex can (after separation of non-complexed antigen) be determined chemiluminometrically in a qualitative, and quantitative way.

The invention also relates to the use of acridinium compounds represented by formula 1 in immunoassays by way of chemiluminescence and energy transfer.

Herein the antibody is coupled to an energy acceptor e.g. a fluorogenic compound, whereafter the antigen-antibody complex can be determined by chemiluminescence and energy transfer without the necessity of separating the non-complexed antigen. The compounds according to the invention are extremely suitable for this kind of assay method because the energy transfer from the acridinium part to an acceptor is very efficient, and because there is no donor (the acridine compound)-acceptor dissociation during the chemiluminescence reaction.

The invention further relates to compounds represented by formula 1, coupled to compounds involved in immunological reactions.

The invention also relates to the use of the above-mentioned coupling products of the acridinium compounds represented by formula 1 with substances which are involved in immunological reactions, for determining immune reactions and immune compounds by means of chemiluminescence whether or not in combination with energy transfer.

BRIEF DESCRIPTION OF THE DRAWINGS

FIG. 1 shows a chemical reaction scheme wherein acridinium compounds according to formula 2 react with hydrogen peroxide, and then exhibit chemiluminescence.

FIG. 2 shows a chemical reaction scheme wherein acridinium compounds of formula 1 react with hydrogen peroxide, and then exhibit chemiluminescence.

FIG. 3 shows a dose-response curve for acridinium ester A.

EXAMPLES

Example 1

Preparation of phenyl acridine-9-carboxylate

Acridine-9-carboxylic acid (5 g) is suspended in thionyl chloride (75 ml). The mixture is stirred under reflux for four hours. The excess of thionyl chloride is removed by distillation. The residue is suspended in pyridine (75 ml) and the mixture stirred at room temperature for ten minutes. Phenol (4.5 g) is added to the suspension. The resulting reaction mixture is stirred at room temperature for sixteen hours. The resulting solution is poured into one normal hydrochloric acid (200 ml). The precipitate that forms (6.5 g) is isolated by filtration, and recrystallized from benzene/cyclohexane. m.p. 192° C.; IR (KBr): 1750, 1177 cm$^{-1}$. MS: 299, 206, 178, 152, 151. $^1$H-NMR: δ7.5–8.5.

Example 2

Preparation of 4-methoxyphenyl acridine-9-carboxylate

This compound is prepared according to example 1 by substituting phenol with 4-methoxyphenol. m.p. 202.4–203° C. $^1$H-NMR: δ3.86, 6.9–8.3. MS 329, 206, 178.

Example 3

Preparation of 4-chlorophenyl acridine-9-carboxylate

This compound is prepared according to example 1 by substituting phenol with 4-chlorophenol. m.p. 169.6–170.2° C. $^1$H-NMR: δ7.3–8.4. MS: 333, 206, 178.

Example 4

Preparation of 4-acetylphenyl acridine-9-carboxylate

This compound is prepared according to example 1 by substituting phenol with 4-hydroxyacetophenone. m.p. 214.2–214.8° C. $^1$H-NMR: δ2.69, 7.5–8.3. MS: 341, 206, 178.

Example 5

Preparation of 2,5-dimethylphenyl acridine-9-carboxylate

This compound is prepared according to example 1 by substituting phenol with 2,5-dimethylphenol. m.p. 187–190° C. $^1$H-NMR: δ2.3, 2.4, 7.0–8.4. MS: 327, 206, 178.

Example 6

Preparation of 1,1,1,3,3,3-hexafluoro-2-propyl acridine-9-carboxylate

This compound is prepared according to example 1 by substituting phenol with 1,1,1,3,3,3-hexafluoro-2-propanol. m.p. 143.2–145° C. $^1$H-NMR: δ6.0–6.5, 7.4–8.3. IR: 2988, 1782, 1200–1000 cm$^{-1}$. MS: 373, 206, 178.

Example 7

Preparation of 2,7-dimethoxyacridine-9-carboxylic acid

A solution of 4,4'-dimethoxydiphenylamine (7.45 g) in dichloromethane (75 ml) is added dropwise to a stirred solution of oxalylchloride (4.68 g) in dichloromethane (50 ml). The reaction mixture is refluxed for twenty minutes, and evaporated. The residue (10.06 g) is dissolved in dichloromethane (100 ml). To this stirred solution, aluminum trichloride (18.16 g) is added in small portions. After the addition is complete the mixture is refluxed for fifty minutes. The solvent is removed, and the residue poured into a mixture of ice/one molar hydrochloric acid (1/1, 300 ml). A red-brown product is collected by filtration. This product is dissolved in ten percent aqueous potassium hydroxide (100 ml), refluxed overnight, and after cooling to room temperature poured into ice/five molar hydrochloric acid (3/1, 500 ml). The yellow crystals of 2,7-dimethoxyacridine-9-carboxylic acid are collected by filtration. The crude product is purified by acidifying a basic (KOH) solution (methanol). Yield 8.03 g (86%). m.p. >290° C. $^1$H-NMR: δ10.5, 7.2–8.6, 3.95. IR: 3526, 2835, 1614 cm$^{-1}$. MS: 283, 268, 240, 196, 169.

Example 8

Preparation of phenyl 2,7-dimethoxyacridine-9-carboxylate

This compound is prepared according to example 1 by substituting acridine-9-carboxylic acid with 2,7-dimethoxyacridine-9-carboxylic acid. $^1$H-NMR: δ3.98, 7.5–8.2. IR: 2838, 1738, 1619, 822 cm$^{-1}$. MS: 359, 266, 238.

Example 9

Preparation of N-phenyl-N-p-toluenesulfonyl acridine-9-carboxamide

This compound is prepared according to example 1 by substituting phenol with N-phenyl-N-p-toluenesulfonamide. NMR: δ6.98–8.12, 2.54. MS: 452, 298, 206, 178, 151, 91.

Example 10

Preparation of N-2-chlorophenyl-N-p-toluenesulfonyl acridine9-carboxamide

This compound is prepared according to example 1 by substituting phenol with N-2-chlorophenyl-N-p-toluenesulfonamide. m.p. 244.5° C. NMR: δ6.5–8.5, 2.38.

Example 11

Preparation of N-4-methoxyphenyl-N-p-toluenesulfonyl acridine-9-carboxamide

This compound is prepared according to example 1 by substituting phenol with N-4-methoxyphenyl-N-p-toluenesulfonamide. m.p. 192.8° C. NMR: δ6.25–8.15, 3.50, 2.57. MS: 482, 328, 206, 178, 151.

Example 12

Preparation of N-2,5-dichlorophenyl-N-p-toluenesulfonyl acridine-9-carboxamide

This compound is prepared according to example 1 by substituting phenol with N-2,5-dichlorophenyl-N-p-toluenesulfonamide. NMR: δ7.0–8.3, 2.38.

Example 13

Preparation of N-3-chloro-5-methylphenyl-N-p-toluenesulfonyl acridine-9-carboxamide This compound is prepared according to example 1 by substituting phenol with N-3-chloro-5-methylphenyl-N-p-toluenesulfonamide.

Example 14

Preparation of N-2-methoxyphenyl-N-p-toluenesulfonyl acridine-9-carboxamide

This compound is prepared according to example 1 by substituting phenol with N-2-methoxyphenyl-N-p-toluenesulfonamide. NMR: δ6.6–8.4, 3.63, 2.34.

Example 15

Preparation of N-4-methoxyphenyl-N-4-nitrophenylsulfonyl acridine-9-carboxamide

This compound is prepared according to example 1 by substituting phenol with N-4-methoxyphenyl-N-4-nitrophenylsulfonamide. NMR: δ6.5-8.3, 3.71.

Example 16

Preparation of N-4-nitrophenyl-N-p-toluenesulfonyl acridine-carboxamide

This compound is prepared according to example 1 by substituting phenol with N-4-nitrophenyl-N-p-toluenesulfonamide. NMR: δ7.0–8.5, 2.6.

Example 17

Preparation of t-butyl iodoacetate

A mixture of t-butyl chloroacetate (20 g) and sodium iodide (25 g) is stirred in acetone (200 ml) for twenty hours. The acetone is removed by distillation under reduced pressure. The residue is partitioned between diethyl ether (100 ml) and water (50 ml). The ether layer is washed with water, 5% sodium thiosulfate solution, and water. The organic layer is dried over sodium sulfate, and evaporated under reduced pressure. There is obtained 25 grams of t-butyl iodoacetate. NMR: δ3.5, 1.38.

Example 18

Preparation of benzyl iodoacetate

This compound is prepared according to example 17 starting from benzyl chloroacetate.

Example 19

Preparation of t-butyl 3-iodopropionate

A mixture of 3-chloropropionyl chloride (20 g), pyridine (20 g), and t-butanol (20 g) in dichloromethane (200 ml) is stirred at room temperature for twenty hours. The reaction mixture is poured into water (200 ml). The organic phase is washed with water, 0.1 molar hydrochloric acid, water, and 5% sodium hydrogencarbonate. After drying over sodium sulfate the organic solvent is removed by distillation under reduced pressure. Part of the residue (5 g) is dissolved in acetone (10 ml), and treated with a solution of sodium iodide (8 g) in acetone. The reaction is refluxed and stirred for twenty hours. Work-up as described in example 17 yields 6.5 grams of t-butyl 3-iodopropionate.

Example 20

Preparation of 9-phenoxycarbonyl-10-carboxymethylacridinium bromide

A mixture of phenyl acridine-9-carboxylate (100 mg) and t-butyl iodoacetate is stirred and heated at 110° C. for five hours. The resulting solution is poured into diethyl ether (25 ml) and the resulting precipitate isolated by filtration. Part of this precipitate (10 mg) is stirred with 33% hydrobromic acid in acetic acid (1 ml), and heated at 50° C. for two hours. The reaction mixture is poured into water, and the resulting precipitate (ca. 6 mg) isolated. MS: 358, 314, 300, 237, 220, 206.

Example 21

Preparation of 9-phenoxycarbonyl-10-carboxyethylacridinium bromide

A mixture of phenyl acridine-9-carboxylate (100 mg) and t-butyl 3-iodopropionate (5 g) is stirred and heated at 130° C. for sixteen hours. The resulting solution is poured into benzene (25 ml) and the resulting precipitate isolated by filtration. Part of this precipitate (10 mg) is stirred with 33% hydrobromic acid in acetic acid (1 ml), and heated at 50° C. for two hours. The reaction mixture is poured into water, and the resulting precipitate (ca. 6 mg) isolated.

Example 22

Preparation of 10-carboxymethyl-9-N-phenyl-N-p-toluenesulfonylcarbamoyl-acridinium bromide This compound is prepared according to example 20 by substituting phenyl acridine-9-carboxylate with N-phenyl-N-p-toluenesulonyl acridine-9-carboxamide. NMR: δ6.8–9.1, 6.61, 2.55. MS: 511, 357, 237.

Example 23

Preparation of 10-carboxymethyl-9-N-2-chlorophenyl-N-p-toluenesulfonylcarbamoyl-acridinium bromide (acridinium compound B)

This compound is prepared according to example 20 by substituting phenyl acridine-9-carboxylate with N-2-chlorophenyl-N-p-toluenesulfonyl acridine-9-carboxamide. NMR: δ6.9–8.8, 6.45, 2.5.

Example 24

Preparation of 10-carboxymethyl-9-phenoxycarbonyl-2,7-dimetioxyacridinium bromide This compound is prepared according to example 20 by substituting phenyl acridine-9-carboxylate with phenyl 2,7-dimethoxyacridine-9-carboxylate.

Example 25

Chemiluminescence of 9-phenoxycarbonyl-10-carboxymethylacridinium bromide (acridinium ester A)

A stock solution containing 0.1 mg of acridinium ester A in methanol (1 ml) is prepared. This stock solution is diluted further in 0.001 molar hydrochloric acid. The chemiluminescence that occurs when this diluted solution is treated with basic hydrogen peroxide (this reagent is freshly prepared by diluting 100 microliters of 5 molar aqueous sodium hydroxide and 20 microliters of 30% hydrogen peroxide in 20 ml of water) is measured using a LUMAC Biocounter 2010. A dose-response curve is obtained as indicated in FIG. 3.

Example 26

Labelling of ovalbumin using activated 10-carboxymethyl-9-N-2-chlorophenyl-N-p-toluenesulfonylcarbamoyl-acridinium bromide Acridinium compound B (1 mg) is dissolved in dimethylformamide (DMF, 0.05 ml). To this solution is added N-hydroxysuccinimide (0.5 mg) and a solution of dicyclohexylcarbodiimide (DCC) in DMF (0.1 g/ml, 0.015 ml). The mixture is incubated at 6° C. for twenty hours giving the labelling solution. Ovalbumin (1 mg) is dissolved in labelling buffer (0.1 M phosphate buffer pH 8.0, 0.1 ml), and treated with labelling solution (0.01 ml). After two hours the labelled protein is separated from the free label by gel filtration over Sephadex G 25. The eluted fractions are analyzed chemiluminometrically.

Example 27

Labelling of human IgG using activated 10-carboxymethyl-9-N-2-chlorophenyl-N-p-toluenesulfonylcarbamoyl-acridinium bromide This labelling is performed as described for the labelling of ovalbumin in example 26. A dilution curve of labelled human IgG, prepared in PBS buffer pH 7.0 did not show any alteration upon standing at room temperature after 24 hours.

We claim:

1. Acridinium compound for use as a chemiluminogenic label, of the formula (1):

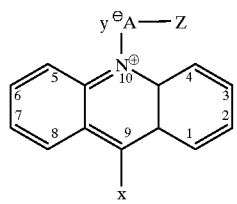 (1)

where
- A is a divalent organic moiety which may contain one or more heteroatoms and/or carbonyl groups, the nature and length of A being such as to allow the functional group Z to react with a biologically active or a toxicologically active compound;
- X is a substituent capable of forming a dioxetane with the accridine C-9 atom upon reaction with hydrogen peroxide, wherein X is selected from the group consisting of alkoxycarbonyl and aryloxycarbonyl groups, wherein X does not contain a functional group capable of coupling with a biologically active or a toxicologically active compound;
- Y is a counter ion; and
- Z is a functional group capable of coupling with a biologically active or a toxicologically active compound, wherein Z is selected from the group consisting of carboxyl group, a reactive derivative of carboxyl group, isocyanate, isothiocyanate, activated halide, derivatives of sulfonic acid, derivatives of phosphoric acid, azides, protonated carboximidate and amino groups, and wherein the acridinium compound may carry one or more substituents selected from the group consisting of a lower alkyl group, a lower alkoxy group and a halogen at any of positions 1 through 8.

2. Acridinium compound according to claim 1, wherein A is an alkylene group having 1–4 carbon atoms.

3. Acridinium compound according to claim 1, wherein Z is a carboxyl group or a reactive derivative thereof.

4. Acridinium compound according to claim 1, wherein the biologically active or toxicologically active compound is an antibody or an antigen.

5. Acridinium compound for use as a chemiluminogenic label, of the formula (1):

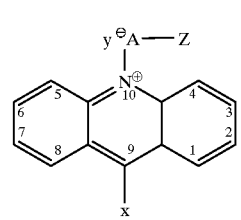 (1)

wherein
- A is an alkylene group having 1–4 carbon atoms;
- X is a substituent capable of forming a dioxetane with the acridine C-9 atom upon reaction with hydrogen peroxide, wherein X is an arylsulfonylcarbamoyl group, and wherein X does not contain a functional group capable of coupling with a biologically active or a toxicologically active compound;
- Y is a counter ion; and
- Z is a carboxyl or a reactive derivative thereof;

and wherein the acridinium compound may carry one or more substituents selected from the group consisting of a lower alkyl group, a lower alkoxy group and a halogen at any of positions 1 through 8.

* * * * *

UNITED STATES PATENT AND TRADEMARK OFFICE
CERTIFICATE OF CORRECTION

PATENT NO. : 6,018,047
DATED : January 25, 2000
INVENTOR(S) : Zomer et al.

It is certified that error appears in the above-identified patent and that said Letters Patent is hereby corrected as shown below:

<u>Title page,</u>
Below "*Primary Examiner* - Mary E. Ceperly" insert the following line,
-- *Attorney, Agent or Firm* — Baker & Botts LLP --.

Item [57], ABSTRACT,
Line 3, "divalcnt" should read -- divalent --, "moicty" should read -- moiety -- and "alkylcnc" should read -- alkylene --

<u>Column 1,</u>
Line 53, "F" should be deleted.
Line 54, "örster" should read -- Förster --.

<u>Column 4,</u>
Line 53, "rcaction" should read -- reaction --, "hydrogcn" should read -- hydrogen --, "pcroxidc" should read -- peroxide -- and "whcrcin" should read -- wherein --.

<u>Column 6,</u>
Line 22, "arc" should read -- are --, "collcctcd" should read -- collected --, "Thc" should read -- The -- and "crudc" should read -- crude --.
Line 44, "acridine9" should read -- acridine 9 --.

<u>Column 8,</u>
Line 25, "7-dimetioxyacridinium" should read -- 7dimethoxyacridinium --.

<u>Column 9,</u>
Lines 4-7,

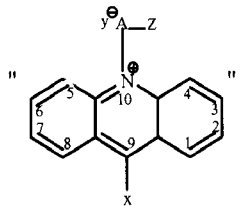

should read

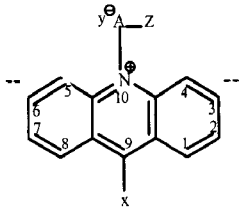

UNITED STATES PATENT AND TRADEMARK OFFICE
CERTIFICATE OF CORRECTION

PATENT NO. : 6,018,047 B1
DATED : January 25, 2000
INVENTOR(S) : Zomer et al.

It is certified that error appears in the above-identified patent and that said Letters Patent is hereby corrected as shown below:

Column 9 cont'd,
Line 13, "where" should read -- wherein --.
Line 20, "accridine" should read -- acridine --.

Column 10,
Lines 11-14,

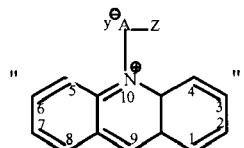

should read

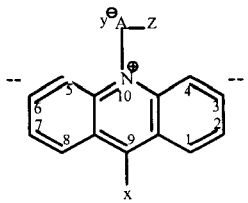

Signed and Sealed this

Twenty-first Day of January, 2003

JAMES E. ROGAN
*Director of the United States Patent and Trademark Office*